United States Patent [19]

Jennings et al.

[11] 4,356,170
[45] Oct. 26, 1982

[54] IMMUNOGENIC POLYSACCHARIDE-PROTEIN CONJUGATES

[75] Inventors: Harold J. Jennings, Ottawa, Canada; Czeslaw Lugowski, Wroclaw, Poland

[73] Assignee: Canadian Patents & Development Ltd., Ottawa, Canada

[21] Appl. No.: 267,440

[22] Filed: May 27, 1981

[51] Int. Cl.³ .......................................... A61K 39/385
[52] U.S. Cl. ............................... 424/92; 260/112 R; 260/121; 424/85; 424/87; 424/88; 424/89; 424/90; 424/91
[58] Field of Search ............ 260/112 R, 121; 424/85, 424/88, 89, 87, 90, 91, 92

[56] References Cited

U.S. PATENT DOCUMENTS

| | | | |
|---|---|---|---|
| 3,847,890 | 11/1974 | Green et al. | 260/112 R X |
| 3,947,352 | 3/1976 | Cuatrecasas et al. | 260/112 R X |
| 4,003,792 | 1/1977 | Mill et al. | 260/112 R X |
| 4,093,607 | 6/1978 | Sela et al. | 260/112 R X |
| 4,125,492 | 11/1978 | Cuatrecasas et al. | 260/112 R X |
| 4,185,090 | 1/1980 | McIntire | 260/112 R X |
| 4,203,893 | 5/1980 | Pery et al. | 260/121 |
| 4,259,232 | 3/1981 | Carrico et al. | 260/112 R |
| 4,303,638 | 12/1981 | Tayot et al. | 424/92 X |
| 4,308,254 | 12/1981 | Tayot et al. | 424/92 X |
| 4,310,514 | 1/1982 | Durette | 424/89 X |
| 4,315,913 | 2/1982 | Durette | 424/88 |

OTHER PUBLICATIONS

Archives of Biochemistry & Biophysics, vol. 181, 1977, Schwartz et al., pp. 542-549.

Primary Examiner—Howard E. Schain
Attorney, Agent, or Firm—Alan A. Thomson

[57] ABSTRACT

Antigenic polysaccharides are modified to generate a terminally-located aldehyde group by controlled oxidation of vicinal hydroxyl groups, e.g. of unlinked terminal non-reducing sialic acid residues. In some cases where there is a reducing end group, e.g. of the type N-acetylmannosamine residue, it can be made into the most susceptible site for oxidation by initially reducing it to its open chain hydroxyl form, e.g. N-acetylmannosaminitol. The vicinal hydroxyl oxidation is controlled to yield a reactive aldehyde group which is then covalently linked to a free amino group of a selected protein by reductive amination. The resulting polysaccharide-protein conjugates are soluble and have been found to have enhanced antigenicity compared to the polysaccharide alone. This terminal aldehyde:free amine group reductive amination can be applied to various polysaccharide antigens and various well-tolerated proteins, preferably protein immunogens. For example, meningococcal group A, B and C polysaccharides have been linked to tetanus toxoid to give soluble conjugates which have been found to have advantageous immunogenic properties.

26 Claims, No Drawings

IMMUNOGENIC POLYSACCHARIDE-PROTEIN CONJUGATES

FIELD OF THE INVENTION

This invention relates to antigenic polysaccharide-protein conjugates, their preparation and use as vaccines. A novel conjugate linkage has been utilized which minimizes cross-linking and gives a soluble conjugate. Animal tests have shown enhanced immunogenic properties for the conjugate compared to the initial polysaccharide antigen. The resulting vaccines are particularly suitable for immunizing human infants against infections, the immune response for which is non-thymus-controlled.

BACKGROUND AND PRIOR ART

Polysaccharides, particularly the capsular polysaccharides from bacteria such as Neisseria meningitidis, have been used with some success in providing homologous serogroup immunity. Meningococcal polysaccharide group A and C are relatively poor immunogens in human infants, and group B is only poorly immunogenic in man. The poor results with infants is highly undesirable since this section of the population has the highest incidence of these infections. In order to surmount these problems with infants and to expand the usefulness of polysaccharide vaccines, it is necessary to enhance the immunogenicity. One possible method of achieving this objective, which has shown some promise, is to conjugate these polysaccharides to a carrier protein. Several instances of this approach have been reported but the coupling methods employed resulted in linkages having highly undesirable structural features for use in human vaccines.

See: (1) W. E. Paul, D. H. Katz, and B. Benacerraf, "Augmented ant-SIII antibody responses to an SIII-protein conjugate", J. Immunol. 107, 685, 1971;

(2) O. T. Avery and W. F. Goebel, "Chemo-immunological studies on conjugated carbohydrate-proteins. V. The immunological specificity of an antigen prepared by combining the capsular polysaccharide III pneumococcus with foreign protein", J. Exp. Med. 54, 437, 1931; and (3) R. J. Fielder, C. T. Bishop, S. F. Grappel, and F. Blank, "An immunogenic polysaccharide-protein conjugate", J. of Immunol. 105, 265, 1970.

These references, (1) and (2) effected diazotization of an aminophenolglycoside forming an azo compound with the protein. Reference (3) utilized cyanuric chloride to form an ether linkage to the protein. Others have recently reported the use of coupling techniques which formed linkages with more acceptable structural features. See: (4) E. C. Beuvery and F. Van Rossum "Characteristics of capsular polysaccharide (PS)-toxoid conjugates", Proceedings of the Third International Conference on Immunity and Immunization in Cerebrospinal Meningitis, In press, 1979; (5) E. C. Beuvery, F. Miedema, R. W. Van Delft and J. Nagel, "Meningococcal group C polysaccharide/tetanus toxoid conjugate as immunogen", Proceedings of the International Symposium on Bacterial Vaccines, In press, 1980; (6) R. Schneerson, O. Barrera, A. Sutton, and J. B. Robbins, "Preparation, characterization, and immunogencity of Haemophilus influenza Type b polysaccharide-protein conjugates", J. Exp. Med. 152, 361, 1980; and (7) S. B. Svenson and A. A. Lindberg, "Immunochemistry of Salmonella O-antigens: preparation of an octasaccharide-bovine serum albumin immunogen representative of Salmonella sero-group B O-antigen and characterization of the antibody response", J. of Immunol. 120, 1750, 1978. References (4), (5) and (7) used water-soluble carbodiimide reagents and formed amido linkages to the protein. Reference (6) carried out a more complex procedure including activation of the polysaccharide with cyanogen bromide, first conjugation of the protein with adipic hydrazide, then treating the mixture with a water-soluble carbodiimide; to form an amido type linkage to the protein and a complex variety of linkages from the adipic spacer to the polysaccharide. These previous methods either (a) utilized many randomly activated functional groups (hydroxyl or carboxylate) on the various polysaccharides leading to considerable crosslinking and poorly defined, low solubility conjugates; (b) required a specific functionality of limited applicability; (c) resulted in less incorporation of polysaccharide than was desired; or (d) led to extraneous modification of the polysaccharide which would alter its antigenicity.

Relatively small disaccharides have been conjugated to protein via their terminal hemiacetal groups using sodium cyanoborohydride reagent. See: (8) B. A. Schwartz and G. R. Gray, Arch. Biochem. Biophys. 181, 542–49, 1977. When we attempted to apply this technique to the high molecular weight meningococcal polysaccharides, unsatisfactory incorporation resulted.

SUMMARY OF THE INVENTION

We have found it possible to introduce a free aldehyde group into the polysaccharide molecule in a terminal location and to specifically couple this aldehyde group to protein without activating other functional groups on the polysaccharide. This procedure avoids crosslinking and extraneous chemical modification of the bulk of the polysaccharide resulting in better defined immunogens.

This invention includes a method of preparing antigenic polysaccharide:protein conjugates, comprising:

(a) providing an antigenic polysaccharide which has reactive vicinal hydroxyl groups in a terminal portion of the molecule;

(b) subjecting said vicinal hydroxyl groups at a terminal location to controlled oxidation to generate a reactive aldehyde group therefrom on the polysaccharide;

(c) selecting a physiologically tolerated protein having a free amino group and reacting said amino group with said aldehyde group by reductive amination, to covalently link said polysaccharide and protein; and (d) recovering a substantially non-crosslinked, soluble, antigenic polysaccharide:protein conjugate.

Another part of the invention is the antigenic-polysaccharide:protein conjugate wherein the polysaccharide and protein are covalently linked through a

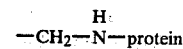

linkage to a terminal portion of the polysaccharide without significant cross-linking, said antigenic polysaccharide having a MW above about 2000.

The invention further includes a vaccine comprising at least one of said conjugates, particularly a vaccine for human infants, and a method of immunizing with said vaccines.

DETAILED DESCRIPTION

Various antigenic polysaccharides may be used according to this invention, the only requirement being that they contain vicinal hydroxyl groups in a terminal portion of the molecule. In particular, capsular polysaccharides from bacteria are most suitable for vaccine purposes. In some cases, unlinked terminal non-reducing sialic acid residues are present in the polysaccharide and they contain suitable vicinal hydroxyl groups. Polysaccharides which initially have a terminal reducing sugar residue can be subjected to a controlled reduction to generate reactive vicinal hydroxyl groups from this terminal residue. One particular example of such a reducing sugar residue is the N-acetylmannosamine residue. Other examples of such residues include those of glucose, glucosamine, rhamnose, and ribose. Antigenic polysaccharides which are particularly useful include those derived from meningococci, *Haemophilus influenza*, pneumococci, β-hemolytic streptococci and *Escherichia coli*. The polysaccharide MW suitably is within about 2,000-100,000 for best coupling and antigenicity.

The reduction of the terminal reducing sugar residues is suitably effected using a mild reducing agent, e.g. sodium borohydride or its equivalent at a pH of about 7.5 to 10. Preferably NaBH$_4$ is used at a pH of 8–9 to minimize side reactions.

It has been found possible to selectively oxidize the terminal vicinal hydroxyl groups to form a terminal aldehyde group by controlled oxidation. This oxidation may be effected conveniently with periodate reagent for a limited time. For instance, approximately 10 mg of polysaccharide suitably is oxidized with about 1 ml of approximately 100 mM sodium metaperiodate solution for about 10–15 min. at room temperature. The reaction time can be varied to accomodate other amounts of periodate to obtain equivalent oxidation. The vicinal hydroxyl groups are cleaved to leave the terminal —CHO group on the polysaccharide.

The protein component may be any physiologically tolerated protein having a free amino group. Preferably, the protein is itself an immunogen. Suitable proteins include tetanus toxoid, diphtheria toxoid and other proteins derived from bacteria. It is possible that other proteins containing lysine residues, e.g. a synthetic polylysine may be useful in a particular system. The bacterial source may be, e.g. β-hemolytic streptococci, *Haemophilus influenza*, meningococci, pneumococci and *E. coli*. If desired, both polysaccharide and protein can be derived from the same bacteria to give a stronger immunogenic effect. The toxoids of tetanus and diphtheria have been approved for human use, and tetanus toxoid was used in the examples. However, other proteins would be operative.

The reductive amination covalently couples the terminal aldehyde group of the polysaccharide to a free amino group on the protein through a

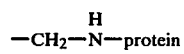

linkage where the —CH$_2$— derives from the aldehyde group. There is no significant cross-linking by this method and the conjugates are water-soluble to a considerable extent. A cyanoborohydride reagent may be utilized to effect this reductive amination. The amount of cyanoborohydride is not critical. Typical amounts may range from about 30 to 100% by wt. based on the polysaccharide. Suitably, the temperature is within about 15° to 40° C. and the reaction is substantially complete in about 10 to 15 days.

The resulting conjugates are useful as vaccines or as components in multiple vaccines. Of particular interest are vaccines for human infants where the initial nonconjugated polysaccharide is of the type for which the immune response is non-thymus-controlled. In this case, the polysaccharide per se is non-immunogenic in infants, but the conjugate of this invention has been found to have properties leading to a thymus-controlled immune response. In particular, enzyme-linked immunosorbent assays (ELISA) have shown high titers of antibody protein in antiserum specific for the polysaccharide in the polysaccharide:protein conjugate utilized. Thus, a vaccine for infants comprising a meningococcal polysaccharide:protein conjugate would be advantageous to protect infants who are most susceptible to meningoccal infection. Such a conjugate could be added to the composite vaccine usually administered to young infants. Advantageous influenza and pneumonia vaccines could also be prepared by this route. Veterinary vaccines against, for example *E. coli* infections in piglets, etc., advantageously would comprise an *E. coli* conjugate of this invention. Desirably both polysaccharide and protein would be from *E. coli*.

The vaccines including one or more conjugates comprise a liquid carrier such as physiological saline, or other injectable liquids. Additives customarily used in such vaccines may be present, e.g. stabilizers such as lactose or sorbitol, and adjuvants such as aluminum hydroxide, sulfate or phosphate, an alum or an alginate. Precipitated AlPO$_4$ is very suitable.

These vaccines may be administered by injection, usually intramuscularly or subcutaneously. For the human infant, the dosage of conjugate normally will be within the range of about 5 to about 25 micrograms. Based on this range, equivalent dosages for higher body weights can be derived. A series of doses may be given for optimum immunity. Dosage unit forms of the vaccine can be provided with amounts of conjugate equivalent to from about 5 to about 25 micrograms based on the human infant.

The following examples are illustrative.

EXAMPLE 1

Reduction of the group A polysaccharide

Meningococcal group A polysaccharide (average m.w. 25,000) (200 mg) was dissolved in 20 ml of water to which 100 mg of NaBH$_4$ was added. The pH was adjusted continuously to 8–9 with diluted H$_2$SO$_4$. The reduction mixture was left overnight at room temperature and was then dialysed against water and dialysate was subsequently lyophilized to yield 180 mg of the reduced group A polysaccharide. This reduced polysaccharide now had a more easily oxidizable terminal vicinal hydroxyl moiety.

Selective periodate oxidation of the polysaccharide

Selected molecular size fractions of the meningococcal native group B (average m.w. 10,000), group C (average m.w. 40,000) and the reduced group A (average m.w. 25,000) polysaccharides were oxidized with 100 mM NaIO$_4$ (sodium metaperiodate) solution (10 mg polysaccharide/1 ml) at room temperature in the dark for 15 min. Following this period, 2 ml of ethylene glycol was added to expend the excess NaIO$_4$ and the solution was left at room temperature for an additional 60 min. The oxidized group A and C polysaccharides were dialysed, lyophilized, and purified by gel-filtration [Sephadex (trademark) G-100 column]. The group B polysaccharide was purified by the direct application of the ethylene glycol-treated reaction mixture to a Sephadex G-25 column. All the oxidized polysaccharides were recovered in 80-90% yields having undergone no significant diminution in molecular size from the original polysaccharide. Each oxidized polysaccharide had an identical elution volume to the latter on the same calibrated columns previously used for the molecular weight determinations of the original native polysaccharides. The oxidized polysaccharides now had a terminally-located aldehyde group.

Direct conjugation of the polysaccharides with proteins

The oxidized polysaccharides (70-100 mg) were added to 4.5-7.5 mg of tetanus toxoid TT or bovine serum albumin BSA solutions in 1-2 ml of 0.25 M $K_2HPO_4$ (pH 9.0) for the group A polysaccharide and 0.75 M $K_2HPO_4$ (pH 9.0) for the group B and C polysaccharides. The variation in the ionic strength of the buffer was used to suppress the formation of insoluble precipitates formed by ionic associations between the polysaccharides and the proteins. Sodium cyanoborohydride (20-40 mg) was added to the solutions followed by 3 drops of toluene and the reaction mixtures were magnetically stirred in sealed vials for 10-15 days at 40° C. The reaction mixtures were then applied directly to Sephadex G-100 columns and the highest molecular weight fraction of each was collected and concentrated by ultrafiltration. The concentrated conjugates were then analysed for their polysaccharide and protein contents. The results indicated that the yield of conjugate as in the case of all the conjugates described herein was in excess of 90% in terms of the total protein content.

The structure of the group C polysaccharide is such that one might expect some of its internal C7-C8 bonds to be readily cleaved by periodate oxidation whereas in actual fact the oxidation of the vicinal 7- and 8-hydroxyl groups of the 9-linked sialic acid residues has been found to be extremely slow. In addition, the polysaccharide is further stabilized by O-acetyl substituents strategically located on many of these same vicinal hydroxyls. However, the oxidation of the same 7- and 8-hydroxyl groups of the unlinked terminal non-reducing sialic acid residue is extremely fast and, as we have found, generates an aldehyde group at C7 of this residue. It is unlikely that the reducing terminal sialic acid residue at the opposite end would oxidize to any great extent using these conditions because it exists in solution mainly in its pyranose ring form and as such has been found to behave similarly to an interchain residue. The group B polysaccharide has similar properties in relation to its periodate oxidation as that of the group C polysaccharide except that the interchain 2→8-linkages make the interchain sialic acid residues even more stable. Thus the aldehyde group was also generated at C-7 of the non-reducing end-group sialic acid residue of the group B polysaccharide.

The structure of the group A polysaccharide presented a different situation to both the group B and C polysaccharides in that its non-reducing N-acetylmannosamine end-group was no more susceptible to periodate oxidation than any of the non-O-acetylated internal residues. However, the reducing end-group N-acetylmannosamine residue was made into the most susceptible residue by simply reducing it to its open chain N-acetylmannosaminitol derivative. In this form, the modified group A polysaccharide was selectively oxidized at this residue to generate a terminally-located aldehyde group. Gel-filtration of all the above polysaccharides before and after oxidation indicated that oxidation had caused no significant diminution in the molecular sizes of these polysaccharides and, therefore, that only minimal interchain breakage could have occurred. Results are summarized in Table 1.

EXAMPLE 2

Immunological properties of the meningococcal conjugates Immunization of rabbits.

The group A, B and C polysaccharide-TT conjugates were used as immunogens in rabbits and the antisera were evaluated by quantitative precipitin and immunodiffusion analysis. The precipitin curves obtained from each of the above antisera, when treated with its homologous TT-conjugates, indicated that a good antibody response was obtained using all three TT-conjugates. This was also confirmed by immunodiffusion experiments where each of the TT-conjugates also gave a strong precipitate with its homologous antiserum. In addition, this latter analysis was also able to further differentiate the antibody response and to identify antibodies of differing specificities in each conjugate. The group A- and C-TT conjugates gave similar results in that both yielded antisera which gave a precipitin line with both their homologous conjugates and their respective homologous polysaccharides. Spurring between these lines in the case of group A also indicated that antibodies specific for TT were also present. The group B polysaccharide-TT conjugate antiserum proved to be an exception to the above examples because although it precipitated with the homologous conjugate it gave no precipitin line with the homologous polysaccharide. However, the fact that antibodies with specificities for other than TT were present was indicated by the fact that a similarly linked group B polysaccharide-BSA conjugate also gave a strong precipitin line using the same antiserum. This result suggested that the determinant responsible for the production of these latter antibodies was situated at the common linkage site (lysine to C7 of the terminal non-reducing heptulosonic acid residue) of both conjugates. This was confirmed by inhibition experiments when a similarly linked group B polysaccharide-lysine conjugate proved to be the most powerful inhibitor of the anti-group B polysaccharide-TT conjugate serum-group B polysaccharide-BSA conjugate system. The ability of the oxidized polysaccharide to inhibit the above precipitation more efficiently than the native group B polysaccharide is also consistent with the above evidence. The fact that the native polysaccharide does inhibit the above precipitation, albeit weakly, also indicates the presence of antibodies which retain some group B polysaccharide specificity. In all cases (groups A, B and C) the control anti-polysaccharide rabbit serum failed to precipitate with its homologous polysaccharide.

EXAMPLE 3

Immunization of mice.

The meningococcal group A, B and C polysaccharide and their TT-conjugates were subcutaneously injected in mice at weekly intervals and seven days following each injection the sera were evaluated for antibody (IgG) levels to the conjugates using the homologous polysaccharide-TT conjugates as coating antigens in the enzyme-linked immunosorbent assay (ELISA) technique (A. Voller, C. C. Draper, D. E. Bidwell and A. Bartlett, "Microplate enzyme-linked immunosorbent assay for Chagas disease", Lancet. 1, 426, 1975). Whereas the sera of the mice repeatedly immunized with the polysaccharides showed no significant increase in antibody level over that of the preimmune sera, that of the mice immunized with each of the conjugates had attained substantially increased antibody levels following the third immunization. The evaluation of one typical serum from a mouse injected with the group C-TT conjugate was carried out. This particular serum was evaluated by coating the wells with the homologous conjugate, the homologous native polysaccharide, and a 2→9 α-D-linked sialic acid oligosaccharide-BSA conjugate. The reciprocal end-point titers indicated that there was a marked increase in the titer of the post immune serum over that of the preimmune serum. The relatively higher titer associated with the group C-TT conjugate over that of its native polysaccharide is consistent with the formation of antibodies associated with the TT moiety.

Bactericidal assays of the mouse antisera produced by the subcutaneous injection of mice with the group A and C polysaccharide-TT conjugates demonstrated the development of significant bactericidal activity following the third injection. While the preimmune sera gave no significant bactericidal titer, the group A-TT conjugate induced in the mice a titer of 1/64 while the group C-TT conjugate induced in the mice a titer of 1/4,096. No bactericidal activity was detected in the mouse antisera produced to the group B-TT conjugate.

The serological experiments using the above conjugates indicated that the polysaccharides of groups A and C had been successfully converted to thymic-dependant immunogens. In their conjugated forms the immunogenicities of both these polysaccharides were substantially increased in rabbits and mice over that of their native polysaccharides. In addition, the presence of antibodies with a specificity for TT were also detected in the antisera from the above experiments. The potential of the group A and C polysaccharide-TT conjugates for use as human vaccines is best demonstrated in the serological results obtained by their weekly subcutaneous injection in mice. Following the third injection, both the group A- and C-TT conjugates had elicited the development of high-titer polysaccharide-specific antisera which also proved to be bactericidal for their respective homologous group A and C organisms.

We claim:

1. A method of preparing antigenic polysaccharide: protein conjugates, comprising:
   (a) providing an antigenic polysaccharide which has reactive vicinal hydroxyl groups in a terminal portion of the molecule and has a MW above about 2000;
   (b) subjecting said vicinal hydroxyl groups at a terminal location to controlled oxidation only sufficient to generate a terminal reactive aldehyde group therefrom on the polysaccharide;
   (c) selecting a physiologically-tolerated protein having a free amino group and reacting said amino group with said aldehyde group by reductive amination, to covalently link said polysaccharide and protein; and
   (d) recovering a substantially non-crosslinked, soluble, antigenic polysaccharide:protein conjugate.

2. The method of claim 1 wherein the antigenic polysaccharide is selected from the group derived from meningococci, *Haemophilus influenza*, pneumococci, β-hemolytic streptococci, and *E. coli*.

3. The method of claim 1 wherein the protein is selected from the group consisting of tetanus toxoid, diphtheria toxoid, and immunogenic proteins derived from bacteria selected from β-hemolytic streptococci, *Haemophilus influenza*, meningococci, pneumococci, and *E. coli*.

4. The method of claim 1 wherein the polysaccharide initially has no terminal vicinal hydroxyl groups but has a terminal reducing sugar residue which is reduced to form reactive vicinal hydroxyl groups in (a).

5. The method of claim 4 wherein the sugar residue is N-acetylmannosamine residue.

6. The method of claim 4 wherein the reduction is effected using sodium borohydride at a pH of about 7.5–10.

7. The method of claim 6 wherein the pH is about 8–9.

8. The method of claim 1 wherein the controlled oxidation in (b) is effected using periodate reagent for a limited time.

9. The method of claim 8 wherein the polysaccharide is derived from meningococci, and the time for controlled oxidation is within 10–15 minutes.

10. The method of claim 1 wherein meningococcal group A, B or C polysaccharides having terminal vicinal hydroxyl groups are utilized and are oxidized sufficiently to convert only the terminal vicinal hydroxyl groups to a terminal aldehyde group, reductive amination carried out to link covalently the terminal aldehyde group to an amino group on the selected protein tetanus toxoid molecule, and recovering a soluble conjugate thereof of enhanced antigenicity.

TABLE 1

Conditions of formation and analyses of the group A, B, C polysaccharide-protein conjugates

| Polysaccharide | M. Wt. of Polysaccharide[a] chosen for conjugation | Molar ratio polysaccharide to protein | Time of reaction (days) | Molarity of phosphate buffer at pH 9.0 | Molar ratio of polysaccharide to TT in conjugate | Molar ratio of polysaccharide to BSA in conjugate |
|---|---|---|---|---|---|---|
| Group A reduced and oxidized | $2.5 \times 10^4$ | 48:1 | 12 d | 0.25 M | 0.4:1.0[b] | — |
| Group B native | $1.0 \times 10^4$ | 68:1 | 11 d | 0.75 M | — | 0.7:1.0[c] |
| Group B oxidized | $1.0 \times 10^4$ | 68:1 | 11 d | 0.75 M | 2.0:1.0[c] | 2.5:1.0[c] |
| Group C oxidized | $4.0 \times 10^4$ | 35:1 | 13 d | 0.75 M | 1.1:1.0[c] | — |

[a]Determined by gel-filtration on Sephadex G-100 or G-50 before and after oxidation
[b]Determined from its phosphate/protein ratio
[c]Determined from its sialic acid/protein ratio 11. An antigenic-polysaccharide:protein conjugate wherein the polysaccharide and protein are covalently linked through a

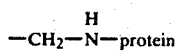

linkage to a terminal portion of the polysaccharide without significant cross-linking, said antigenic polysaccharide having a MW above about 2000.

12. The conjugate of claim 11 wherein the antigenic polysaccharide is selected from the group derived from meningococci, *Haemophilus influenza*, pneumococci, β-hemolytic streptococci, and *E. coli*.

13. The conjugate of claim 11 wherein the protein is selected from the group consisting of tetanus toxoid, diphtheria toxoid, and immunogenic proteins derived from bacteria selected from β-hemolytic streptococci, *Haemophilus influenza*, meningococci, pneumococci and *E. coli*.

14. The conjugate of claim 11 wherein the antigenic polysaccharide is selected from meningococcal Group A, B or C polysaccharides and the protein is tetanus toxoid.

15. The conjugate of claim 11 wherein the antigenic polysaccharide is derived from *Haemophilus influenza* and the protein is tetanus toxoid.

16. The conjugate of claim 11 wherein said linkage is through an end-group terminal reducing sugar moiety on the polysaccharide.

17. The conjugate of claim 16 wherein said reducing sugar moiety is N-acetylmannosaminitol.

18. The conjugate of claim 11 wherein said linkage is through a lysine amino group on the protein.

19. The conjugate of claim 11 wherein the polysaccharide and protein are derived from the same bacteria.

20. A method of immunizing against infection susceptible humans or animals comprising, administering a vaccine comprising the conjugate of claim 11 in an immunogenic amount by intramuscular or subcutaneous injection.

21. The method of claim 20 wherein the dosage of the conjugate is equivalent to from about 5 to about 25 micrograms for the human infant.

22. The method of claim 21 wherein human infants are immunized with a vaccine comprising at least one of (a) the conjugate of meningococcal polysaccharide, and (b) the conjugate of *H. influenza* polysaccharide.

23. A vaccine comprising at least one conjugate as defined in claim 11.

24. A vaccine for infants comprising the conjugate of claim 11 wherein the initial non-conjugated polysaccharide is of the type for which the immune response is non-thymus-controlled.

25. A human infant vaccine comprising the conjugate of claim 11 wherein the polysaccharide comprises at least one of meningococcal polysaccharide and *Haemophilus influenza* polysaccharide.

26. A vaccine as in claim 24 in a dosage unit form wherein the conjugate is present in the equivalent of from about 5 to about 25 micrograms based on the human infant.

* * * * *